United States Patent
Yue et al.

(10) Patent No.: US 10,654,795 B2
(45) Date of Patent: May 19, 2020

(54) METHOD FOR SYNTHESIZING KETOXIME

(71) Applicant: CHEMICAL TECHNOLOGY ACADEMY OF SHANDONG PROVINCE, Jinan (CN)

(72) Inventors: Tao Yue, Jinan (CN); Xu Yang, Jinan (CN); Wenguo Xing, Jinan (CN); Qi Chen, Jinan (CN); Guijun Chen, Jinan (CN); Fujun Lu, Jinan (CN); Weichun Feng, Jinan (CN); Yunge Zhai, Jinan (CN)

(73) Assignee: CHEMICAL TECHNOLOGY ACADEMY OF SHANDONG PROVINCE, Jinan (CN)

( * ) Notice: Subject to any disclaimer, the term of this patent is extended or adjusted under 35 U.S.C. 154(b) by 0 days.

(21) Appl. No.: 16/490,598

(22) PCT Filed: Nov. 1, 2017

(86) PCT No.: PCT/CN2017/108885
§ 371 (c)(1),
(2) Date: Sep. 3, 2019

(87) PCT Pub. No.: WO2018/157617
PCT Pub. Date: Sep. 7, 2018

(65) Prior Publication Data
US 2020/0002270 A1    Jan. 2, 2020

(30) Foreign Application Priority Data
Mar. 3, 2017 (CN) .......................... 2017 1 0123379

(51) Int. Cl.
*C07C 249/14* (2006.01)
(52) U.S. Cl.
CPC .................................. *C07C 249/14* (2013.01)
(58) Field of Classification Search
CPC .................................................... C07C 249/14
See application file for complete search history.

(56) References Cited

U.S. PATENT DOCUMENTS 8,974,673 B2 * 3/2015 Paatero ............... B01F 7/00441
                                                      210/669

FOREIGN PATENT DOCUMENTS

| CN | 1432432 A | 7/2003 |
|---|---|---|
| CN | 1432560 A | 7/2003 |
| CN | 1461747 A | 12/2003 |
| CN | 1687018 A | 10/2005 |
| CN | 1706818 A | 12/2005 |
| CN | 1939897 A | 4/2007 |
| CN | 100386307 C | 5/2008 |
| CN | 103282344 A | 9/2013 |
| CN | 103864643 A | 6/2014 |
| CN | 103896801 A | 7/2014 |
| CN | 106831486 A | 6/2017 |

OTHER PUBLICATIONS

Machine traslation CN103864643, 2015.*

* cited by examiner

*Primary Examiner* — Ana Z Muresan
(74) *Attorney, Agent, or Firm* — Bayramoglu Law Offices LLC

(57) ABSTRACT

A method for synthesizing a ketoxime is provided. In a system of an aqueous carbonate solution, a reaction is performed on a ketone, ammonia and hydrogen peroxide by using a titanium-silicon molecular sieve as a catalyst to obtain the ketoxime. Moreover, a reaction progress is judged and an optimal reaction ratio is determined by a real-time monitoring of a pH value in a reaction system during the reaction. In the present invention, by monitoring the pH value in the reaction system, the progress of the reaction is judged, thereby determining the optimal reaction ratio. The pH of the system is further adjusted by an aqueous carbonate solution to increase the reaction velocity and conversion rate of the ammonia.

9 Claims, 3 Drawing Sheets

METHOD FOR SYNTHESIZING KETOXIME

CROSS REFERENCE TO THE RELATED APPLICATIONS

This application is the national phase entry of International Application No. PCT/CN2017/108885, filed on Nov. 1, 2017, which is based upon and claims priority to Chinese Patent Application No. 201710123379.9, filed on Mar. 3, 2017, the entire contents of which are incorporated herein by reference.

TECHNICAL FIELD

The present invention relates to a synthesis method, and in particular to a method for synthesizing ketoxime, belonging to the technical field of organic synthesis.

BACKGROUND

The existing process of ammoximation reaction requires the addition of a low-carbon alcohol soluble in water, such as t-butanol as a solvent. However, the selected solvent cannot stably exist in the fuming sulfuric acid system, and separation processes, such as multiple distillations, extractions, etc., should be performed before the rearrangement reaction, resulting that the process is complicated, the energy consumption is large, the stability of the oxime solution is poor, etc. The patent CN200510032184 discloses an improved ammoximation technique using a process of integrating two heterogeneous reactions. The solvent used in the Beckmann rearrangement reaction is the same as the solvent used in the oximation reaction. The solvent can stably exist in a rearrangement system containing the fuming sulfuric acid, and doesn't react itself. Therefore, the pure oxime can be obtained from the oximation product without conventional separation methods such as distillation, extraction, etc. However, the method has drawbacks such as unreasonable raw material reaction ratio, serious waste of raw materials, low conversion rate and the like.

In order to solve the problem, such as separation efficiency of the catalyst, etc., in the ammoximation process, the patent CN021002274 and the patent CN021002282 disclose a continuous setting separation method for ammoximation products and the catalyst. The catalyst is recycled, thereby improving the utilization rate of the hydrogen peroxide and realizing the industrialization of the novel process. However, since the silicon and titanium elements in the titanium-silicon molecular sieve catalyst are easily dissolved and lost in the concentrated ammonia solution of the ammoximation reaction, the continuous and stable circulation of the catalyst may be affected. The patent CN031379141 discloses a method for inhibiting the loss of the catalyst and prolonging the service life of the catalyst. A liquid silicon-containing auxiliary agent is added to the ammoximation reaction system including a silicon-containing catalyst to allow the silicon in the solution to achieve an equilibrium concentration, and thus the loss of the silicon in the catalyst is significantly reduced. However, the above method increases the complexity of the reaction, and introduces new impurities, which increases the difficulty of the oximation reaction, and reduces the conversion rate.

In summary, as for the continuous ammoximation process, the following problems are currently presented: (1) the reaction ratio of the raw materials is unreasonable, the waste of the raw materials is serious, and the conversion rate is low; (2) The concentrated ammonia solution in the ammoximation reaction easily causes the dissolution and loss of the active elements in the catalyst, which affects the continuous and stable circulation of the catalyst.

SUMMARY

The objective of the present invention is to provide a method for synthesizing ketoxime to overcome the drawbacks in the above prior art.

In order to achieve the above objective, the following technical solutions are used in the present invention.

A method for synthesizing ketoxime, which is performed in an aqueous carbonate system: performing a reaction on ketone, ammonia and hydrogen peroxide by using a titanium-silicon molecular sieve as a catalyst to obtain the ketoxime; wherein, a reaction progress is judged and an optimal reaction ratio is determined by a real-time monitoring of a pH value in a reaction system during the reaction.

Preferably, specific steps are as follows: gradually introducing a predetermined amount of the ammonia and a non-predetermined amount of the hydrogen peroxide into a three-phase mixed system composed of the ketone, the aqueous carbonate solution and the titanium-silicon molecular sieve, and monitoring the pH value in the reaction system by using an online pH meter; when the pH value returns to an initial pH of the aqueous carbonate solution, stopping dropwise adding the hydrogen peroxide, and after the reaction is completed, putting aside for layering, wherein a product extracted from an upper layer is the ketoxime, and a lower layer is an aqueous phase.

Further preferably, the aqueous carbonate solution is an aqueous solution of sodium carbonate or an aqueous solution of sodium bicarbonate.

Further preferably, the aqueous carbonate solution has a mass concentration of 0.1% to 10%.

Further preferably, a pH of the aqueous solution of sodium bicarbonate is determined by two factors including a side reaction of the ketone and a destruction of the titanium-silicon molecular sieve.

The pH of the aqueous carbonate solution preferably ranges from 9 to 12 and is more preferably 10.

Further preferably, a mass ratio of the ketone, the ammonia, the titanium-silicon molecular sieve and the aqueous carbonate solution is (80-90):10:2:50.

Further preferably, the ammonia is an ammonia gas or a concentrated ammonia solution.

Further preferably, a time of introducing the ammonia is 1 hour.

Further preferably, a temperature of the reaction is 50-70° C., and after stopping dropwise adding the hydrogen peroxide, the reaction is kept at the temperature for 5 hours.

Further preferably, the ammonia is introduced simultaneously with the hydrogen peroxide, and a molar ratio of the hydrogen peroxide to the ammonia is maintained at 1.2:1.

Further preferably, the aqueous phase at the lower layer is continuously used after being partially removed by a rotary evaporation.

The ketone is selected from ketones having a carbon number of equal to or less than 8, and is further preferably acetone, butanone, 2-pentanone, or cyclohexanone.

Preferably, the titanium-silicon molecular sieve is a molecular sieve TS-1 or a molecular sieve TS-2.

The advantages of the present invention are as follows:

In the present invention, the reaction progress is judged by a real-time monitoring of a pH value in a reaction system and thus the optimal reaction ratio is determined, and further, the pH of the system is adjusted by the aqueous carbonate solution to increase the reaction velocity and the conversion rate of the ammonia.

Taking the butanone as an example, in an oximation reaction, when the pH value is less than 10, the hydrogen peroxide and the ketone easily form an ester by an oxygen insertion reaction, reducing the reaction yield; when the pH value is greater than 12, and the catalyst of the titanium-silicon molecular sieve is seriously damaged. A strict control of the side reaction can be achieved by introducing the online pH monitoring of the present invention. Under the premise of the ketone and the ammonia having predetermined amounts, the optimal reaction ratio is determined with the adding amount of the hydrogen peroxide when the pH is 10, which improves the conversion rates of the three main raw materials, especially the ammonia.

Compared with the conventional method for preparing ketoxime, the present invention is advantageous for determining the optimal reaction ratio and improving the material utilization rate. The alkaline system of the aqueous carbonate solution can effectively promote the progress of the ammoximation, thereby increasing the conversion rate of the ammonia and reducing the ammonia concentration required for the system, which effectively reduces the loss of the active elements of the catalyst of the titanium-silicon molecular sieve, and improves the stability of the catalyst recycling. In the present invention, the carbonate solution is employed to maintain the pH value of the reaction system, effectively reducing the occurrence of side reactions. Moreover, in the present invention, the aqueous phase reaction system is employed, avoiding the problems of pollution and separation of organic solvents in traditional oxime chemistry.

DETAILED DESCRIPTION OF THE EMBODIMENTS

The present invention is further described with reference to the accompanying drawings and embodiments. It should be noted that the following description is only used to explain the present invention and is not intended to limit the content thereof.

The reaction equation of the present invention is as follows:

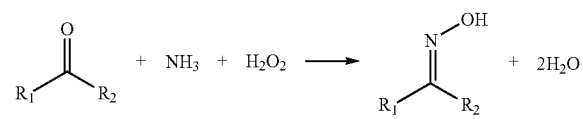

Embodiment 1

Figure 1:
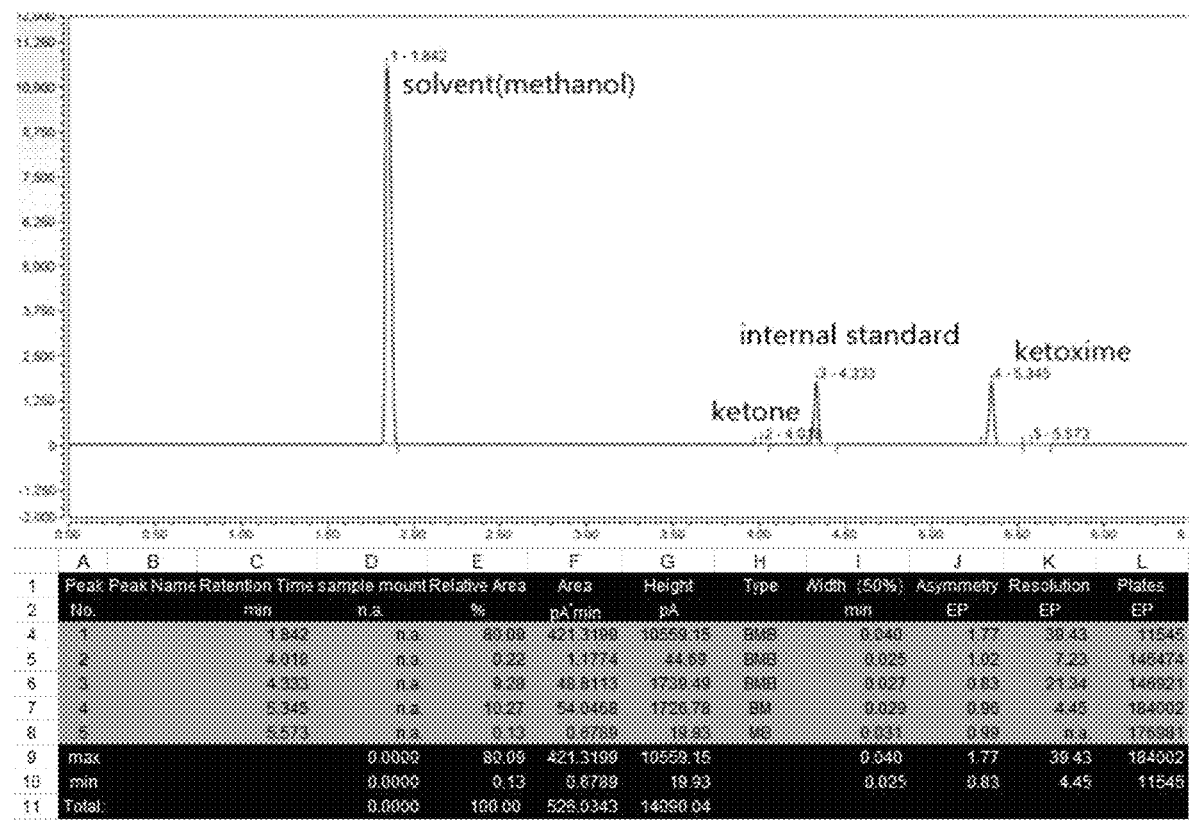
FIG. 1 is a gas chromatogram of a product according to embodiment 1.

First, 50 g of an aqueous solution of $NaHCO_3$ having a pH of 10 was prepared and placed in a three-necked flask, then 2 g of a TS-1 catalyst and 80 g of cyclohexanone were successively added, a water bath temperature was 50° C. and a detection electrode of a pH meter was inserted. After starting a stirring, ammonia gas and hydrogen peroxide were simultaneously introduced, wherein an introducing amount of the ammonia gas was 10 g, and an introducing time was 1 hour; the hydrogen peroxide was introduced at a speed where a molar ratio of the hydrogen peroxide to the ammonia solution was maintained to be 1.2:1 until the pH value returned from 12 in the reaction process to the initial pH value of 10. The temperature was kept on for 5 hours, and then the reaction was stopped. After cooling to room temperature, the light phase in the upper layer was extracted, which was the product oxime, and part of the aqueous phase in the lower layer was discharged to remove 70% of water by a rotary evaporation, and then returned to the reaction kettle for recycle. The gas chromatogram of the product is shown in FIG. 1.

Embodiment 2

First, 50 g of an aqueous solution of $NaHCO_3$ having a pH of 9 was prepared and placed in a three-necked flask, then 2 g of a TS-1 catalyst and 87 g of acetone were successively added, a water bath temperature was 70° C. and a detection electrode of a pH meter was inserted. After starting a stirring, ammonia gas and hydrogen peroxide were simultaneously introduced, wherein an introducing amount of the ammonia gas was 10 g, and an introducing time was 1 hour; the hydrogen peroxide was introduced at a speed where a molar ratio of the hydrogen peroxide to the ammonia solution was maintained to be 1.2:1 until the pH value returned from 12 in the reaction process to the initial pH value of 9. The temperature was kept on for 5 hours, and then the reaction was stopped. After cooling to room temperature, the light phase in the upper layer was extracted, which was the product oxime, and part of the aqueous phase in the lower layer was discharged to remove 70% of water by a rotary evaporation, and then returned to the reaction kettle for recycle.

Embodiment 3

First, 50 g of an aqueous solution of $Na_2CO_3$ having a pH of 12 was prepared and placed in a three-necked flask, then 2 g of a TS-1 catalyst and 90 g of butanone were successively added, a water bath temperature was 50° C., and a detection electrode of a pH meter was inserted. After starting a stirring, ammonia gas and hydrogen peroxide were simultaneously introduced, wherein an introducing amount of the ammonia gas was 10 g, and an introducing time was 1 hour; the hydrogen peroxide was introduced at a speed where a molar ratio of the hydrogen peroxide to the ammonia solution was maintained to be 1.2:1 until the pH value returned from 13 in the reaction process to the initial pH value of 12. The temperature was kept on for 5 hours, and then the reaction was stopped. After cooling to room temperature, the light phase in the upper layer was extracted, which was the product oxime, and part of the aqueous phase in the lower layer was discharged to remove 70% of water by a rotary evaporation, and then returned to the reaction kettle for recycle.

Embodiment 4

First, 50 g of an aqueous solution of $Na_2CO_3$ having a pH of 11 was prepared and placed in a three-necked flask, then 2 g of a TS-1 catalyst and 83 g of 2-pentanone were successively added, a water bath temperature was 60° C. and a detection electrode of a pH meter was inserted. After starting a stirring, ammonia gas and hydrogen peroxide were simultaneously introduced, wherein an introducing amount of the ammonia gas was 10 g, and an introducing time was 1 hour; the hydrogen peroxide was introduced at a speed where a molar ratio of the hydrogen peroxide to the ammonia solution was maintained to be 1.2:1 until the pH value returned from 12 in the reaction process to the initial pH value of 11. The temperature was kept on for 5 hours, and then the reaction was stopped. After cooling to room temperature, the light phase in the upper layer was extracted, which was the product oxime, and part of the aqueous phase in the lower layer was discharged to remove 70% of water by a rotary evaporation, and then returned to the reaction kettle for recycle.

Embodiment 5

First, 50 g of an aqueous solution of $Na_2CO_3$ having a pH of 11 was prepared and placed in a three-necked flask, then 2 g of a TS-1 catalyst and 80 g of cyclohexanone were successively added a water bath temperature was 50° C. and a detection electrode of a pH meter was inserted. After starting a stirring, ammonia gas and hydrogen peroxide were simultaneously introduced, wherein an introducing amount of the ammonia gas was 10 g, and an introducing time was 1 hour; the hydrogen peroxide was introduced at a speed where a molar ratio of the hydrogen peroxide to the ammonia solution was maintained to be 1.2:1 until the pH value returned from 12 to the initial pH value of 11. The temperature was kept on for 5 hours, and then the reaction was stopped. After cooling to room temperature, the light phase in the upper layer was extracted, which was the product oxime, and part of the aqueous phase in the lower layer was discharged to remove 70% of water by a rotary evaporation and then returned to the reaction kettle for recycle.

In order to verify the advantages and effectiveness of the method in the present invention over conventional oximation experimental methods, two conventional experimental methods for preparing ketoxime (without adding the aqueous carbonate solution or using a pH meter to monitor the pH of the system) were added as comparative examples.

Comparative Example 1

Figure 2:
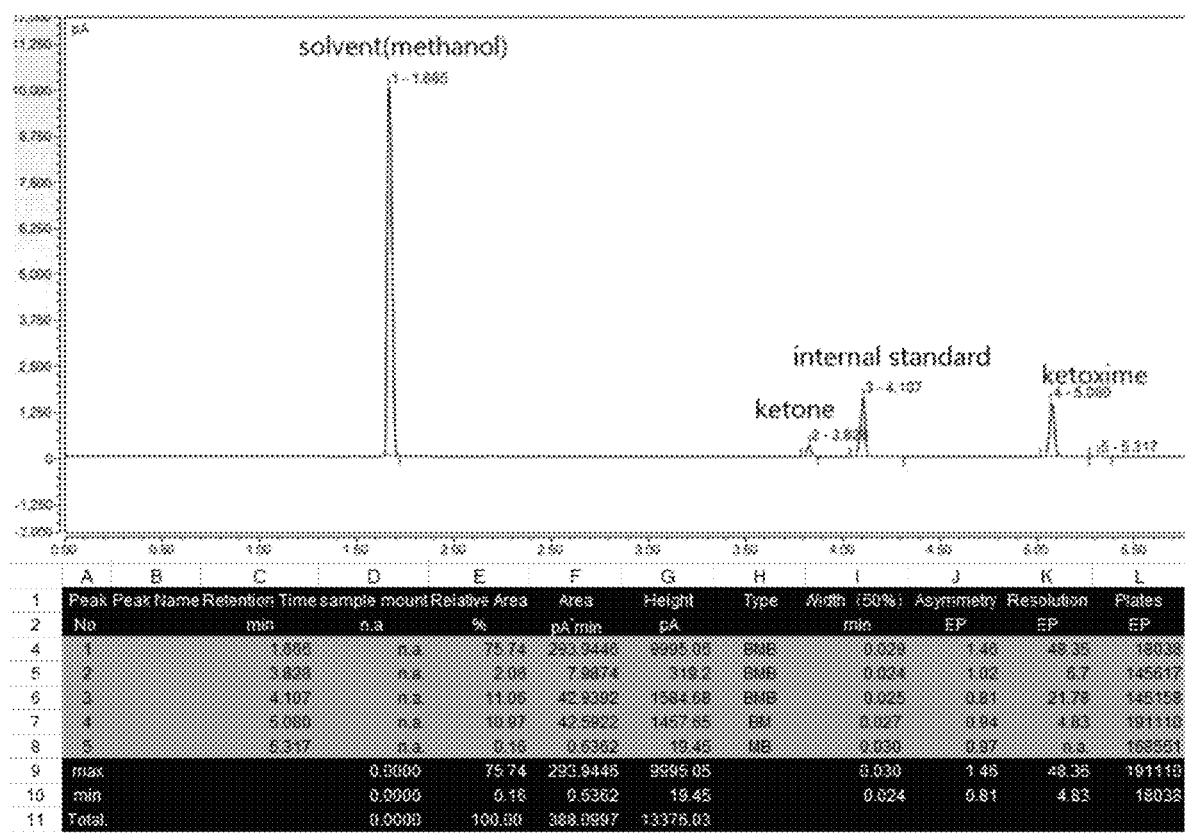
FIG. 2 is a gas chromatogram of a product according to comparative example 1.

2 g of TS-1 catalyst, 80 g of cyclohexanone and 50 g of water were successively added to a three-necked flask and a water bath temperature was 50° C. After starting a stirring, ammonia gas and hydrogen peroxide were simultaneously introduced, wherein an introducing amount of the ammonia gas was 10 g, an introducing amount of the hydrogen peroxide (27%) was 50 g and an introducing time was 1 hour. The temperature was kept on for 5 hours and then the reaction was stopped. After cooling to room temperature, the light phase in the upper layer was extracted, which was the product cyclohexanone-oxime. The gas chromatogram of the product is shown in FIG. 2.

Comparative Example 2

Figure 3:
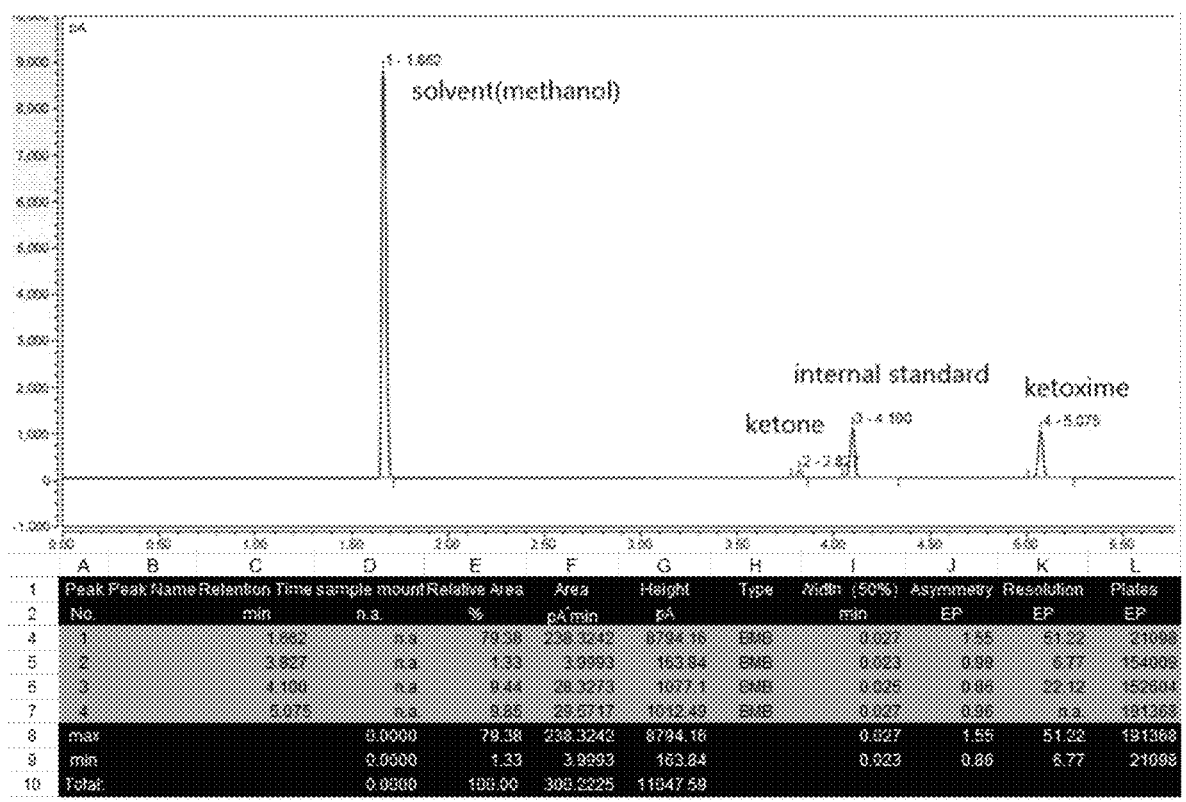
FIG. 3 is a gas chromatogram of a product according to comparative example 2.

2 g of TS-1 catalyst, 80 g of cyclohexanone and 50 g of water were successively added to a three-necked flask and a water bath temperature was 50° C. After starting a stirring, ammonia gas and hydrogen peroxide were simultaneously introduced, wherein an introducing amount of the ammonia gas was 10 g, an introducing amount of the hydrogen peroxide (27%) was 50 g and an introducing time was 1 hour. The temperature was kept on for 5 hours, and then the reaction was stopped. After cooling to room temperature, the light phase in the upper layer was extracted, which was the product cyclohexanone-oxime. The gas chromatogram of the product is shown in FIG. 3.

Test Example

1. Product content test: the products of embodiments 1-5 and comparative examples 1-2 were subjected to quantitative analysis of gas chromatography and the test results are shown in Table 1.

TABLE 1

Test results of contents of products of various embodiments and comparative examples

| Item | Color | Ketone content (%) | Oxime content (%) |
|---|---|---|---|
| Embodiment 1 | Transparent and clarified | 2.3 | 95.1 |
| Embodiment 2 | Transparent and clarified | 2.9 | 93.0 |
| Embodiment 3 | Transparent and clarified | 3.1 | 92.5 |
| Embodiment 4 | Transparent and clarified | 2.8 | 93.1 |
| Embodiment 5 | Transparent and clarified | 7.1 | 90.1 |
| Comparative example 1 | Turbid and yellowish | 14.3 | 81.2 |
| Comparative example 2 | Turbid and yellowish | 10.5 | 85.1 |

2. Raw material conversion rate calculation: the products oximes of embodiments 1-5 and comparative examples 1-2 were subjected to material balance to obtain conversion rates of the three raw materials and the results are shown in Table 2.

TABLE 2

Conversion rate data of each embodiment and comparative example

| Conversion rate | Ketone (%) | Ammonia (%) | Hydrogen peroxide |
|---|---|---|---|
| Embodiment 1 | 95.1 | 87.0 | 90.2 |
| Embodiment 2 | 92.5 | 82.4 | 87.6 |
| Embodiment 3 | 91.8 | 81.9 | 88.6 |
| Embodiment 4 | 90.7 | 81.6 | 85.7 |
| Embodiment 5 | 87.3 | 78.2 | 81.5 |
| Comparative example | 80.3 | 71.9 | 75.8 |
| Comparative example | 84.5 | 73.4 | 79.7 |

The specific embodiments of the present invention have been described with reference to the accompanying drawings above, which are not intended to limit the scope of the present invention. Based on the technical solutions of the present invention, various modifications or variations that can be made by those skilled in the art without any creative effort are still within the scope of the present invention.

What is claimed is:

1. A method for synthesizing a ketoxime, comprising: performing a reaction on a ketone, ammonia and hydrogen peroxide by using a titanium-silicon molecular sieve as a catalyst to obtain the ketoxime in a system of an aqueous carbonate solution;
   wherein a reaction progress is judged and an optimal reaction ratio is determined by a real-time monitoring of a pH value in a reaction system during the reaction, and wherein steps are as follows: gradually introducing a predetermined amount of the ammonia and a non-predetermined amount of the hydrogen peroxide into a three-phase mixed system composed of the ketone, the aqueous carbonate solution and the titanium-silicon molecular sieve, and monitoring the pH value in the reaction system by using an online pH meter; when the pH value returns to an initial pH of the aqueous carbonate solution, stopping dropwise adding the hydrogen peroxide, and after the reaction is completed, putting aside the reaction system for layering, wherein a product extracted from an upper layer of the reaction system is the ketoxime, and a lower layer of the reaction system is an aqueous phase.

2. The method for synthesizing the ketoxime of claim 1, wherein, the aqueous carbonate solution is an aqueous solution of sodium carbonate or an aqueous solution of sodium bicarbonate.

3. The method for synthesizing the ketoxime of claim 2, wherein, a pH of the aqueous solution of sodium bicarbonate is determined by two factors including a side reaction of the ketone and a destruction of the titanium-silicon molecular sieve.

4. The method for synthesizing the ketoxime of claim 1, wherein, the pH value of the aqueous carbonate solution is 9-12.

5. The method for synthesizing the ketoxime of claim 1, wherein, a mass ratio of the ketone, the ammonia, the titanium-silicon molecular sieve and the aqueous carbonate solution is (80-90):10:2:50.

6. The method for synthesizing the ketoxime of claim 1, wherein, a temperature of the reaction is 50-70° C., and after stopping dropwise adding the hydrogen peroxide, the reaction is kept for 5 hours.

7. The method for synthesizing the ketoxime of claim 1, wherein, the ammonia is introduced simultaneously with the hydrogen peroxide, and a molar ratio of the hydrogen peroxide to the ammonia is maintained at 1.2:1.

8. The method for synthesizing the ketoxime of claim 1, wherein, the aqueous phase is continuously applied after being partially removed by a rotary evaporation.

9. The method for synthesizing the ketoxime of claim 1, wherein, the ketone is selected from ketones having a carbon number of equal to or less than 8.

* * * * *